United States Patent [19]

Nakamura et al.

[11] Patent Number: 5,104,379
[45] Date of Patent: Apr. 14, 1992

[54] MEDICAL INSTRUMENT AND VALVE TO BE MOUNTED ON A MOUNT PIECE OF THAT INSTRUMENT

[75] Inventors: Ichiro Nakamura, Kokubunji; Hideki Tujiya, Hachioji, both of Japan

[73] Assignee: Olympus Optical Co., Ltd., Tokyo, Japan

[21] Appl. No.: 500,764

[22] Filed: Mar. 28, 1990

[30] Foreign Application Priority Data

| Apr. 3, 1989 | [JP] | Japan | 1-84447 |
| Aug. 14, 1989 | [JP] | Japan | 1-207849 |
| Sep. 5, 1989 | [JP] | Japan | 1-230133 |
| Feb. 2, 1990 | [JP] | Japan | 62-8946[U] |

[51] Int. Cl.⁵ ............................................ A61M 5/00
[52] U.S. Cl. .............................. 604/111; 604/256; 604/905
[58] Field of Search .............. 604/111, 110, 167, 164, 604/170, 171, 256, 257, 415, 905

[56] References Cited

U.S. PATENT DOCUMENTS

| 3,994,412 | 11/1976 | Difiglio | 604/111 X |
| 4,632,673 | 12/1986 | Tiitola et al. | 604/415 |
| 4,842,591 | 6/1989 | Luther | 604/167 X |
| 4,899,903 | 2/1990 | Miyasaka et al. | 604/111 X |
| 4,909,798 | 3/1990 | Fleischhacker et al. | 604/167 X |

FOREIGN PATENT DOCUMENTS

| 59-133877 | 8/1984 | Japan |
| 62-275447 | 11/1987 | Japan |

*Primary Examiner*—John D. Yasko
*Attorney, Agent, or Firm*—Frishauf, Holtz, Goodman & Woodward

[57] ABSTRACT

A medical instrument whose distal end is inserted into a body cavity of a subject in cooperation with a treating unit, comprises an insertion section including a distal end inserted into the body cavity and having a first opening exposed there, a proximal base end located outside the body of the subject, and a channel provided in the insertion section and extending from the proximal base end toward the first opening, an operation section connected to the proximal base end and having a second opening leading to the channel, a mount piece provided around the second opening. A valve is provided on the mount piece including a body having a slit adapted to be opened when the treating unit is inserted into the channel and closed when it is withdrawn from the channel and an annular groove detachably fitted on the mount piece, and a thin-walled portion for destroying the valve when the valve is removed from the mount piece.

24 Claims, 14 Drawing Sheets

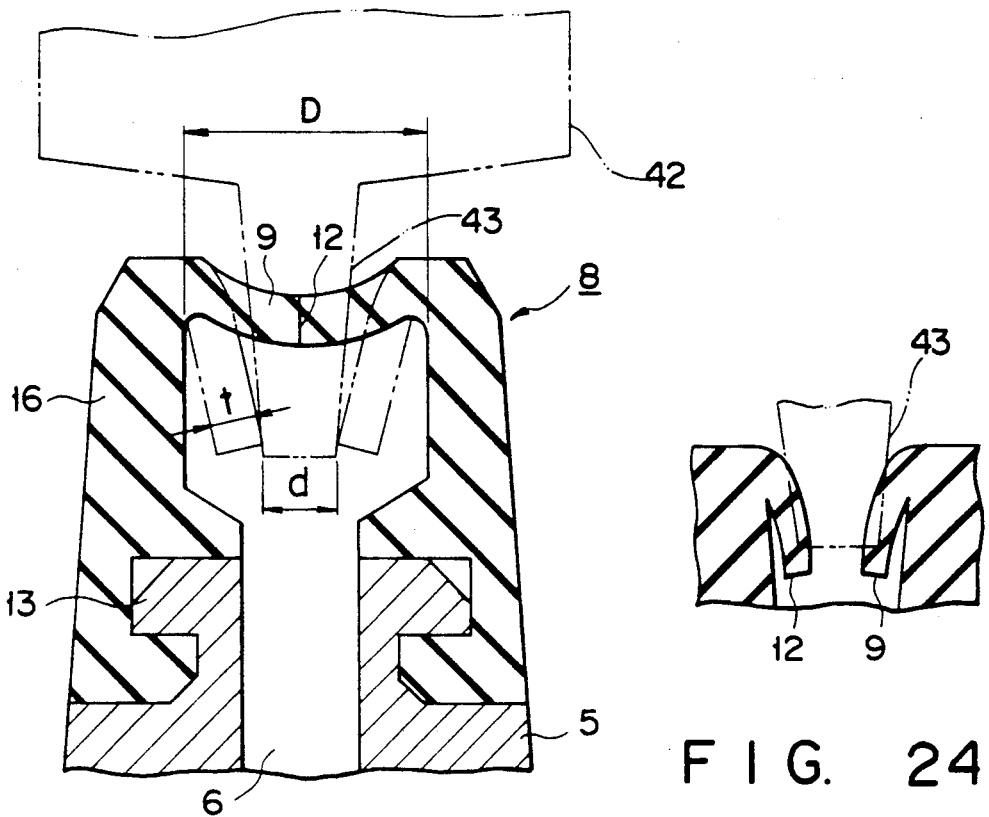
FIG. 23
FIG. 24
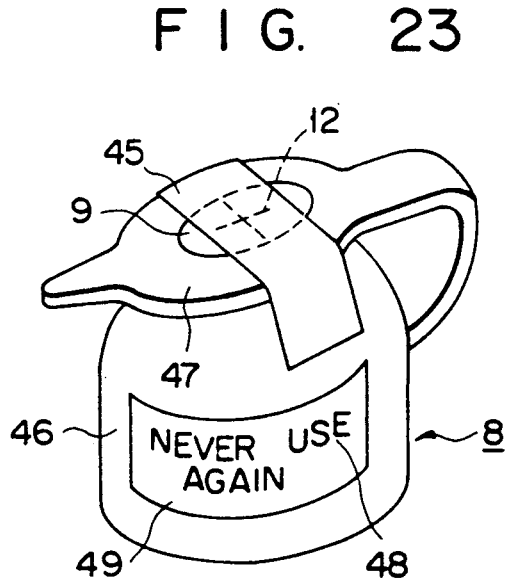
FIG. 25
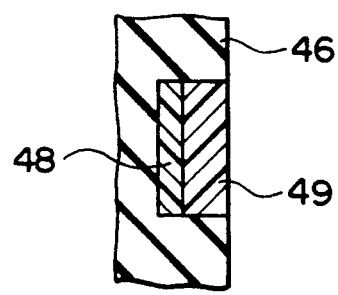
FIG. 26

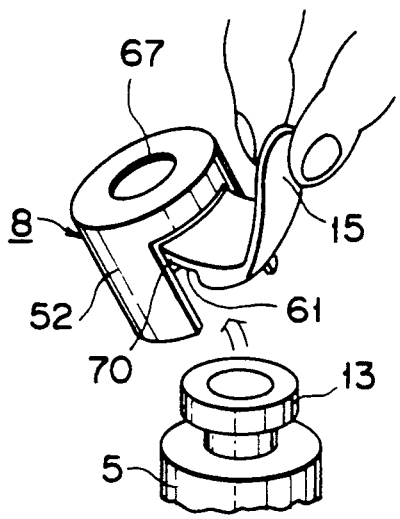
F I G. 34
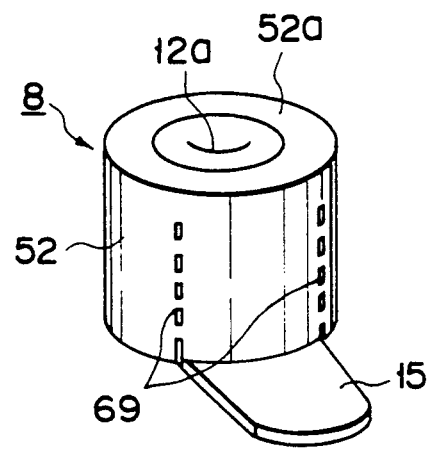
F I G. 35
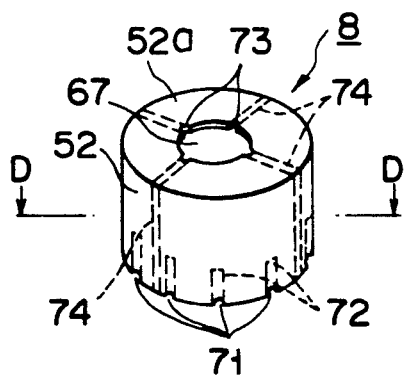
F I G. 36
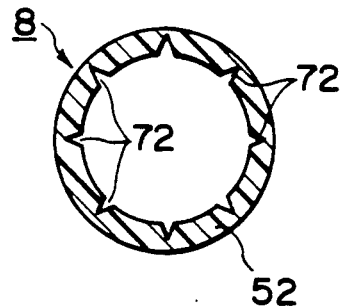
F I G. 37

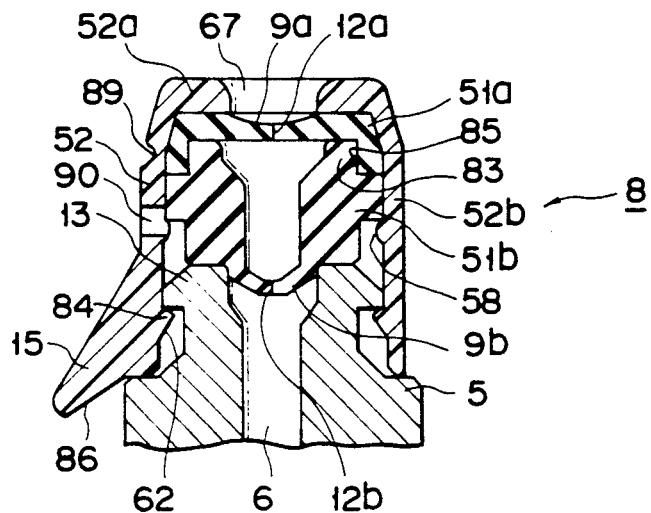
F I G. 41
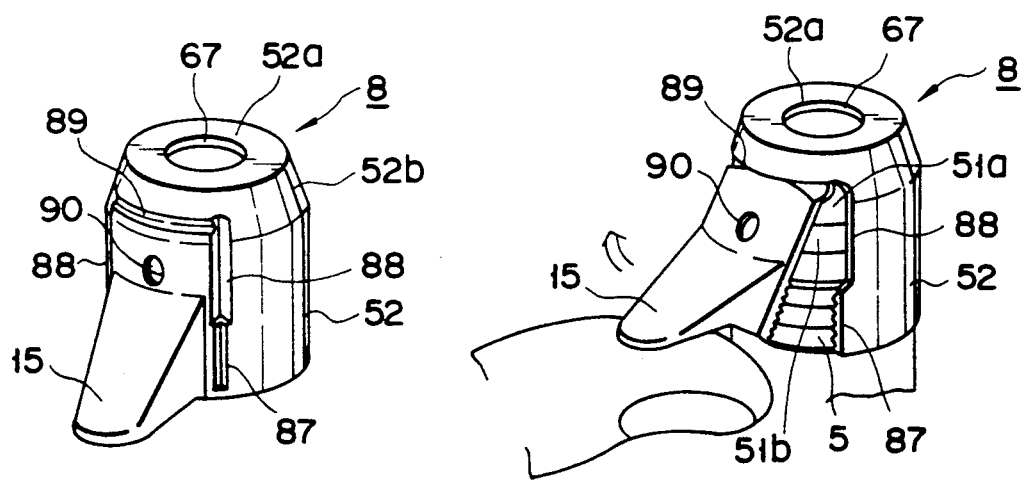
F I G. 42    F I G. 43

MEDICAL INSTRUMENT AND VALVE TO BE MOUNTED ON A MOUNT PIECE OF THAT INSTRUMENT

BACKGROUND OF THE INVENTION

1. Field of the Invention

The present invention relates to a medical instrument whose distal end is inserted into a body cavity of a subject when it is used and to a valve adapted to be fitted over a mount piece of the medical instrument.

2. Description of the Related Art

A technique using a tube insertion guide unit is known which is employed to introduce a catheter for a contrast medium into a body cavity such as a blood vessel. For example, the Published Unexamined Japanese Patent Application 59-133877 discloses a valve which is fitted on the open end of the tube guide unit. The valve is used to prevent an external flow of blood via an internal passage of the guide unit.

Such a valve is required even in a simple catheter so as to prevent an external flow of a fluid.

In an endoscope, a channel tube is used to inject a liquid medicine into the body cavity of a patient or to insert a distal end of a treating instrument, to for example, resect or pick up an affected or diseased region of the patient. During the use of the endoscope, a valve is served to prevent an external leakage of a gas or wastes in the body cavity through the channel tube due to a change in an internal pressure prevalent in the body cavity. The Published Unexamined Japanese Patent Application 62-275447, for example, discloses a sealing valve which is mounted on the opened end of a channel tube of the endoscope.

The valve is made of an elastic material such as rubber and includes a closed film having a slit. A treating unit, such as forceps or catheter, is inserted through the slit of the closed film of the valve into the channel tube. Upon the insertion of the treating unit in this way, the valve seals the inside of the channel against the external endoscope.

In the aforementioned conventional valve assembly, an annular groove provided in the inner wall surface of the valve is fitted over a flange provided on a mounting seat of a mounting mount piece, or a projection provided on the outer periphery of the valve is fitted into an associated annular groove on the inner surface of a mounting mount piece, or the valve is attached by a proper mounting member to the mount piece. The valve can be removed from the associated mount piece by a reversed process without destroying it.

Since, in this way, the valve is attached to and detached from the associated mount piece without destroying it or impairing its function, even if the valve is soiled by a body fluid or partially broken upon the insertion and withdrawal of the treating unit into and away from the channel tube, there is a risk that it will be reused without being aware of these facts.

In the case where the valve has an uneven surface necessary for attachment or detachment to and from an associated mount piece, it is difficult to completely wash away the wastes from the uneven surface of the valve.

In order to avoid a possible risk of a human subject developing an infection or to achieve the accuracy with which a region of interest of the subject is picked up for examination, it is absolutely necessary to replace a "once-used" valve with a new one after a medical examination has been performed.

A valid countermeasure is, therefore, required so that the once-used valve is inadvertently not reused for medical treatment.

SUMMARY OF THE INVENTION

It is accordingly the object of the present invention to provide a valve which, after being fitted over a mount piece, cannot be reused without being broken apart, and a medical instrument equipped with such a valve so that a high sanitary safety can be ensured during use.

The aforementioned object of the present invention can be achieved by a medical instrument or valve as will be set out below. The valve comprises a body made of elastic material and having means adapted to be opened when a medical unit associated with a medical instrument is inserted therethrough and closed when it is removed therefrom, means for detachably fitting the body over a mount piece, and means for destroying the body when the body is removed from the mount piece. In the medical instrument, the valve is fitted over that mount piece which is located outside at an open end of a channel tube when the distal end of the medical instrument is inserted into the body cavity of a human subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 23 is a cross-sectional view showing a state in which a variant of the present invention is fitted over an associated mount piece;

FIG. 24 is a cross-sectional view showing a state in which an insertion portion of a syringe is inserted through a slit of the valve of FIG. 23;

FIG. 25 is a perspective view showing another variant of the present invention;

FIG. 26 is a cross-sectional view showing a display section of the variant of FIG. 25;

FIG. 34 is a perspective view showing a state in which the valve of the eleventh embodiment is removed from the mount piece;

FIG. 35 is a perspective view showing a valve according to a twelfth embodiment of the present invention;

FIG. 36 is a perspective view showing a thirteenth embodiment of the present invention;

FIG. 37 is a cross-sectional view, as taken along line D—D in FIG. 36, showing the valve of FIG. 36;

FIG. 41 is a cross-sectional view showing a valve according to a fourteenth embodiment of the present invention which is fitted over an associated mount piece;

FIG. 42 is a perspective view showing a valve of FIG. 41;

FIG. 43 is a perspective view showing a state in which the valve of FIG. 42 is removed from the mount piece;

DETAILED DESCRIPTION OF THE PREFERRED EMBODIMENTS

The embodiments of the present invention will be explained below with reference to the accompanying drawings.

FIGS. 1 through 5 show an endoscope 1 for medical application, according to a first embodiment of the present invention, and a valve 8 for use in the endoscope.

Figure 1:
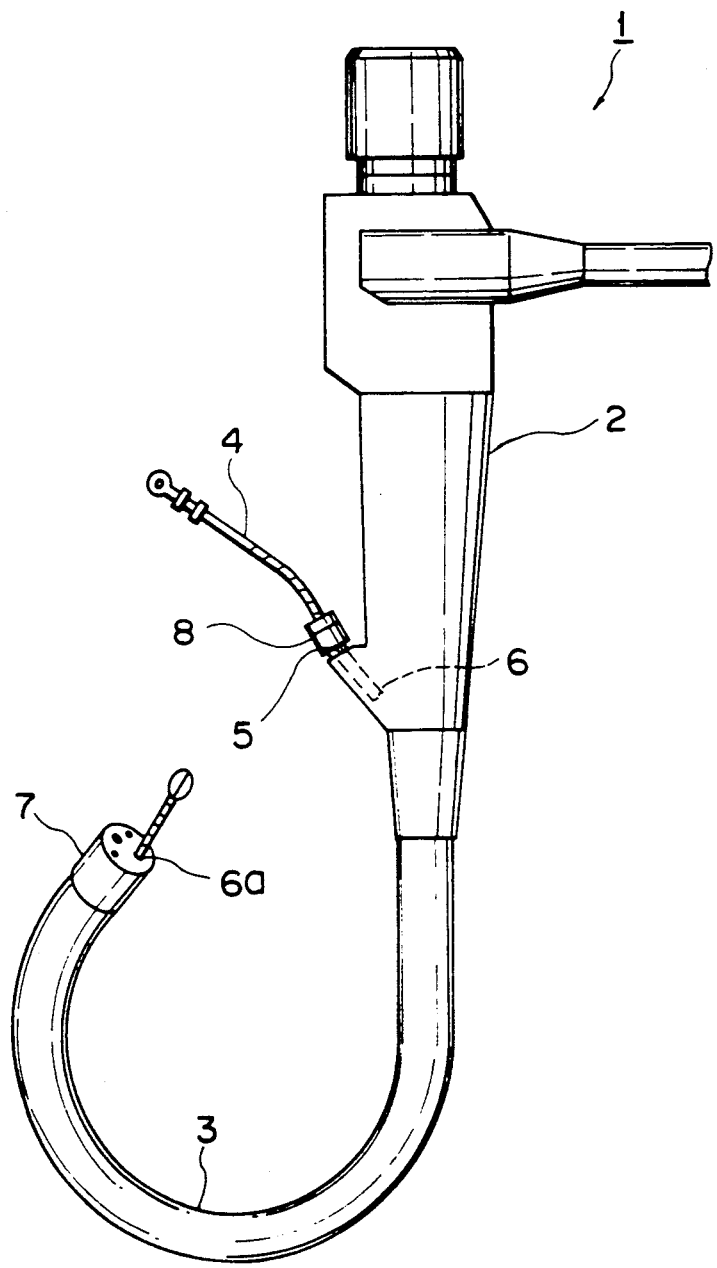
FIG. 1 is a perspective view showing an endoscope using a valve according to a first embodiment of the present invention.

The endoscope 1 shown in FIG. 1 includes an operation section 2 and an insertion section 3. The operation section 2 has a mount piece 5 for use in inserting a treating unit 4, such as forceps, and is connected to a channel tube 6 provided in the insertion section 3 to allow the passage of the insertion section 3. The channel tube 6 is made up of a flexible tube. A distal end 7 of the channel tube 6 is connected to an opening 6a provided at the distal end of the insertion section 3. The treating unit 4, such as forces, is passed through the channel 6 with the forward end of the treating unit 4 extendable out of the open end 6a of the distal end 7 portion of the insertion section 3.

A valve 8 is detachably fitted over the mount piece 5 in an airlight fashion to allow the interior of the insertion channel tube 6 to be hermetically sealed against an external atmosphere. The valve 8 is made of elastic material, such as flexible synthetic resin.

Figure 3:
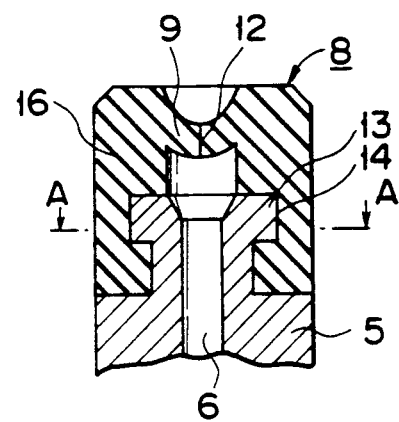
FIG. 3 is a cross-sectional view showing a valve of FIG. 1 which is fitted over an insertion open end of the endoscope.
Figure 4:
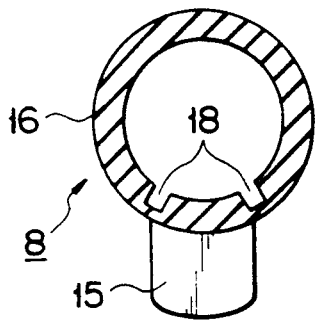
FIG. 4 is a cross-sectional view as taken along line A—A in FIG. 3 in which a mount piece is omitted.

As shown in FIG. 3, the valve 8 is substantially M-shaped in cross-section and has a closed film portion 9 at the outer end of a cylindrical valve section 16 with a slit 12 formed there. A treating unit, such as a syringe, not shown, can hermetically be inserted through the slit 12. An annular groove 14 is provided in the inner peripheral portion of the cylindrical section 16 of the valve 8 to be hermetically fitted over a flange 13 of the mount piece 5.

Figure 2:
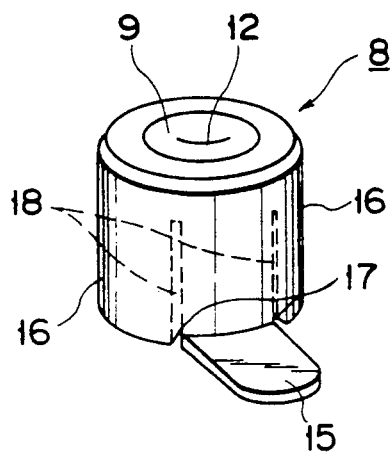
FIG. 2 is a perspective view showing the valve shown in FIG. 1.

As shown in FIG. 2, a tongue-like tab 15 is provided as a finger grip on the lower end of the outer wall of the cylindrical section of the valve 8. The tab 15 is provided integral with the body 16 of the valve 8. A pair of cuts 17 are provided in the end of the body 16 at each side of the base portion of the tab 15 such that a corresponding pair of grooves 18 are provided in the inner wall of the valve body 16 to be joined with the cuts 17. The cuts 17 are continuously formed such that they extend toward a level higher than that of the annular groove 14. The cuts 17 merge with the grooves 18, 18 to provide a pair weakened thin-wall elongated portions for ready breakage. The valve 8, if being pulled by the tab, is broken along the thin-wall portions so that it becomes a useless state.

The operation of the valve 8 will be explained below in more detail.

In use, the valve 8 is fitted over the mount piece 5 of the endoscope as shown in FIG. 3. The treating unit 4 is hermetically inserted past the valve 8 into the channel tube 6.

Figure 5:
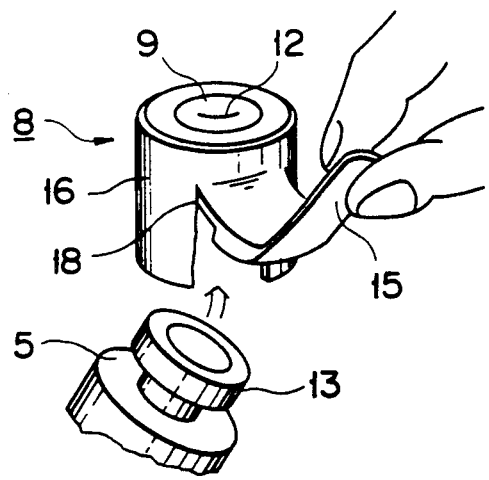
FIG. 5 is a perspective view showing a state in which the valve of FIG. 1 is removed from the insertion open end of the endoscope.

The endoscope 1 is washed clean after it has been used for treatment and, at that time, the valve is removed from the mount piece 5. Upon the removal of the valve 8, the tab 15 is pulled upwardly by the operator's fingers as shown in FIG. 5 at which time the valve 8 is torn apart along the grooves 18 from the cuts 17, causing a breakage of the valve 8. Since the portion of the annular groove 14 into which the flange 13 of the mount piece is fitted is torn apart so that the valve 8 can be detached from the mount piece.

By so doing, the valve 8 can readily be removed from the mount piece 5 of the endoscope. At this time, the valve 8 is destroyed into an unusable state, preventing the used valve from being repetitively employed in an insanitary condition.

Figure 6:
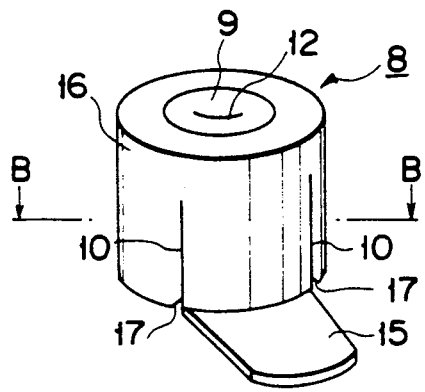
FIG. 6 is a perspective view showing a valve according to a second embodiment of the present invention.
Figure 7:
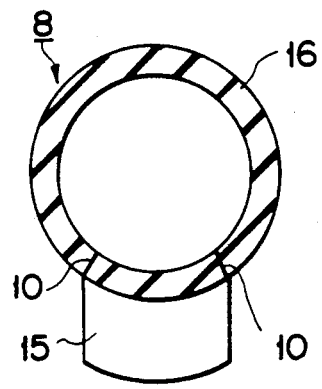
FIG. 7 is a cross-sectional view, as taken along line B—B in FIG. 6, showing the valve of FIG. 6.

FIGS. 6 and 7 show a valve 8 according to a second embodiment of the present invention. In this valve, weakened breaking portions 10 are used, in place of the aforementioned grooves 18, such that they are weakly bonded by a bonding agent on the valve.

Upon the pull of the tab 15 by the operator's fingers, the breaking portions 10 are peeled off along the cuts, causing a breakage of the valve 8. Since a valve portion is torn along the annular groove 14 away from the outer periphery of the flange 13 of the mount piece so that the valve 8 is placed under a readily peelable condition. It is thus possible to readily remove the valve 8 from the mount piece 5. Since the value 8 is destroyed to the extent that it cannot be mounted on the mount piece, it is possible to prevent it from being reused in any insanitary condition and to ensure a sanitary safety.

Figure 8:
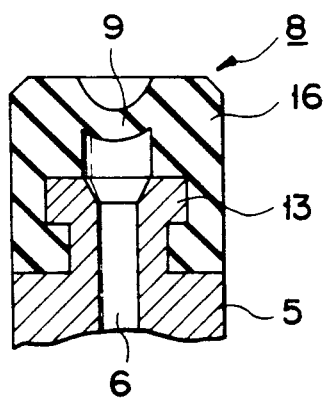
FIG. 8 is a cross-sectional view of a valve according to a third embodiment of the present invention.
Figure 9:
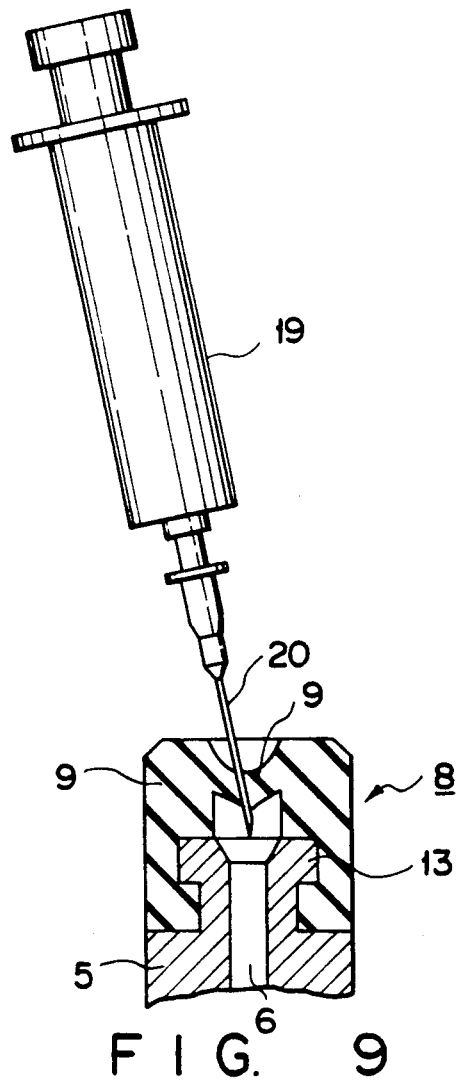
FIG. 9 is a view showing the valve of FIG. 8 and a syringe.

FIGS. 8 and 9 show a valve 8 according to a third embodiment of the present invention. This valve 8 has no slit at its closed film portion 9. The closed film portion 9 allows a needle 20 of a syringe (medical unit) 19 to be hermetically inserted therein.

Figure 10:
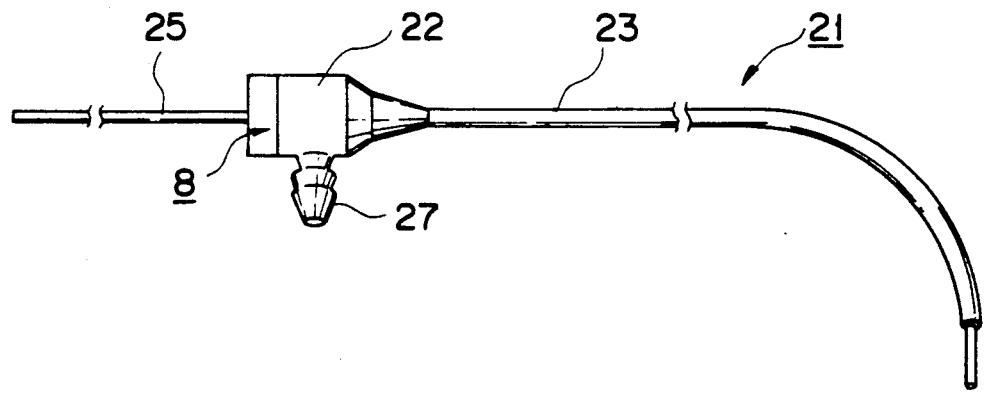
FIG. 10 is a side view showing an insertion guide unit using a valve according to a fourth embodiment of the present invention.
Figure 11:
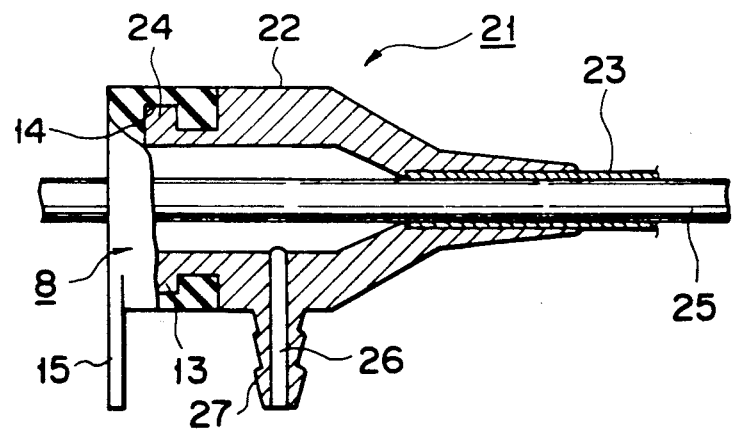
FIG. 11 is a cross-sectional view showing a mount piece of the insertion guide unit of FIG. 10.

FIGS. 10 and 11 show a fourth embodiment of the present invention.

The device of FIGS. 10 and 11 is a medical trochar for introducing a tube, such as a blood vessel catheter, into a human body. A medical guide unit 21, such as a trochar, comprises a substantially cylindrical body 22 and a flexible tube 23 inserted into the cylindrical body 22. A mount piece 24 is formed at the proximal end of the body 22. A valve 8 is fitted over the mount piece 24 which is of such a type as shown in the first embodiment of the present invention.

A passage 26 and connection section 27 are provided at the side wall of the body 22, the passage 26 being used to inject a heparin physiological salt solution into a subject to prevent the thrombus and the connection section 27 being used to enable a tube for liquid supply, not shown, to be connected thereto.

Upon the use of the medical guide unit 21, the distal end of a treating tube, such as a catheter, is inserted through a slit 12 of the valve 8 and guided into a body cavity via a channel tube (an inner cavity of the cylindrical body 22) and flexible tube 23.

After use, the valve 8 is detached from the mount piece for washing. In this case, a tab 15 is pulled apart from the mount piece by the operator's fingers in the same way as shown in FIG. 5. At this time, the valve 8 is torn along the grooves 18, 18 from the cuts 17, 17 and the valve is partly broken at the annula groove 14 fitted over the flange 13. It is thus possible to readily remove the valve 8 from the mount piece 24. That is, a pull of the tab 15 ensures a ready detachment of the valve 8 from the mount piece 24. The valve 8 thus detached is destroyed to an extent that it cannot again be used. This prevents the valve from being reused under an insanitary condition and ensures a sanitary safety against the medical instrument.

Figure 12:
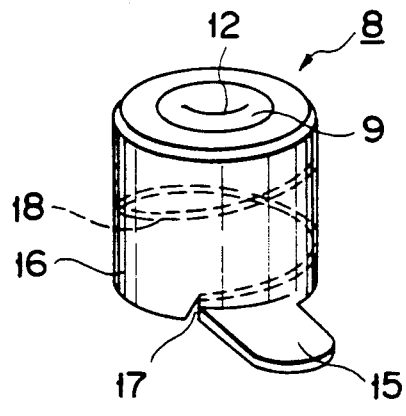
FIG. 12 is a perspective view showing a valve according to a fifth embodiment of the present invention.
Figure 13:
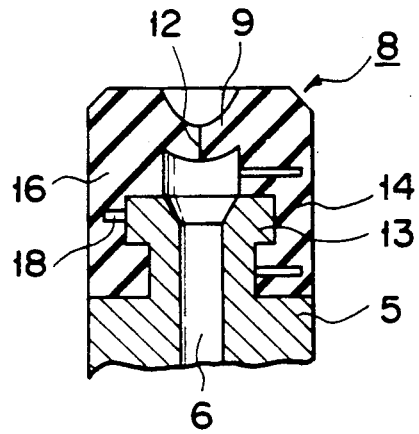
FIG. 13 is a cross-sectional view showing the valve of FIG. 12.

FIGS. 12 and 13 show a valve 8 according to a fifth embodiment of the present invention. This embodiment is similar to the first, second and third embodiments in using the valve 8, but different from the latter in the following respects.

That is, a single cut 17 is provided at a base portion between a tab 15 and a body 16 and a single groove 18 joined with the cut 17 is helically formed in the inner side wall of the body 16 such that it continuously extends up to a level higher than that of an annular groove 18.

Upon a pull of the tab 15 by the operator's fingers as in the preceding embodiment, a valve 8 is helically torn along the groove 18 from the cut 17. At this time, a valve portion is partly broken at the annular groove 14 fitted over the outer periphery of a flange 13 and the valve 8 can readily be torn apart from a mount piece 5 to an extent that it cannot again be used. This prevents the valve 8 from being reused under the insanitary condition and ensures an enhanced sanitary level.

Since, according to the fifth embodiment of the present invention, the groove 18 is helically provided in the inner side wall of the body 16, an added strength acts against a force tending to expand the diameter of the valve 8, upon the mounting of the valve 8 on the mount piece 5, thus preventing an unauthorized breakage of the valve 8 along the helical groove.

Figure 14:
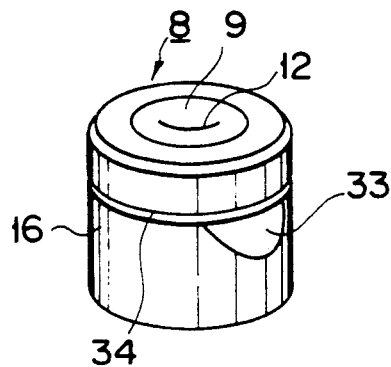
FIG. 14 is a perspective view showing a valve according to a sixth embodiment of the present invention.
Figure 15:
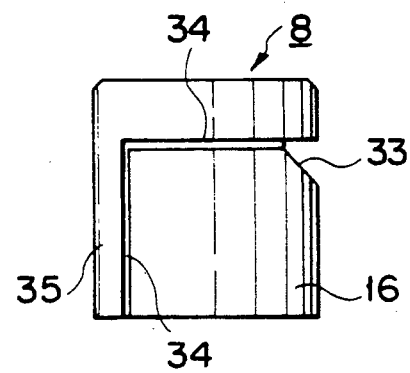
FIG. 15 is a side view showing a valve of FIG. 14.
Figure 16:
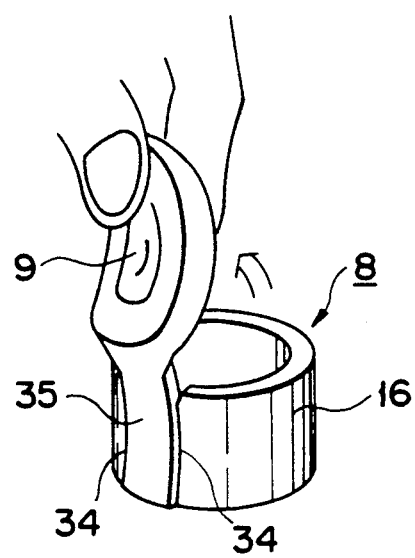
FIG. 16 is a perspective view showing a state in which the valve of FIG. 14 is removed.

FIGS. 14 to 16 show a valve according to a sixth embodiment of the present invention. This valve 8 is of such a type that, as in the aforementioned first embodiment, it is fitted over a mount piece 5, but that a cutout 33 is provided at the upper end of a body 16 to allow the operator's fingers to be grippingly engaged there. A groove 34 merging with the cutout 33 extends along the outer periphery of the body 16 to a location where the end of the groove extends down to the lower end of the body 16 in a substantially symmetrical position to the cutout 33. In this case, a tear band 35 is provided, as a weakened portion, between a pair of downwardly directed grooves 31.

Upon the removal of the valve 8 from the mount piece 5, the operator's fingers are placed in the cutout 33 and the valve 8 is lifted off the mount piece 5, causing the upper portion of the body 16 to be broken. Upon a further pull of the valve 8 with an added strength, the valve 8 is peeled along the grooves of the tear band 35 as indicated by an arrow in FIG. 16 and broken and it is removed from the mount piece 5. It is thus possible to obtain such an advantage as set forth in connection with the aforementioned embodiment.

Figure 17:
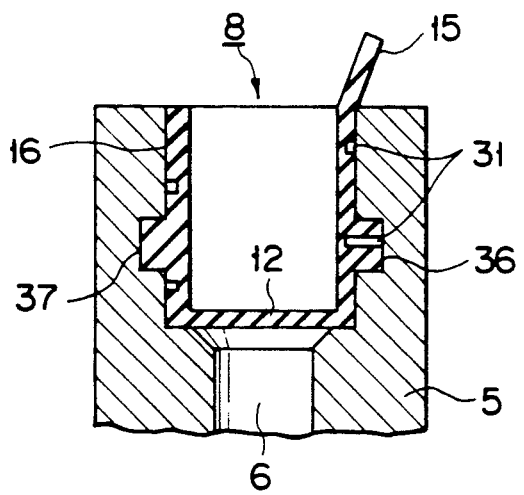
FIG. 17 is a cross-sectional view showing a state in which a valve according to a seventh embodiment of the present invention is fitted over an associated mount piece.
Figure 18:
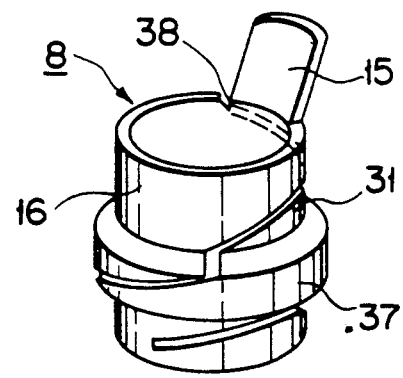
FIG. 18 is a perspective view showing the valve of FIG. 17.
Figure 19:
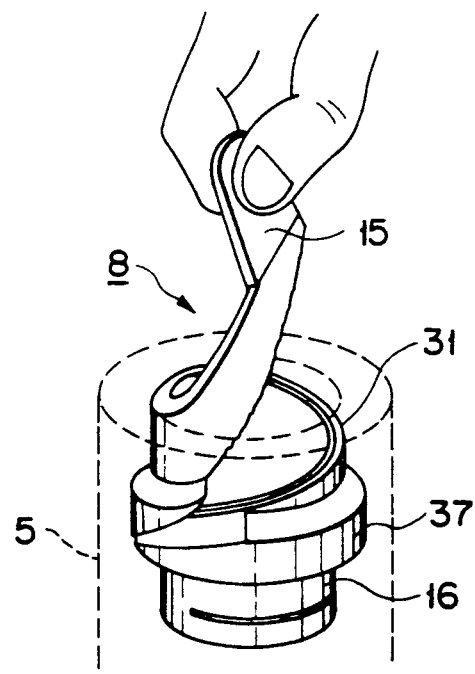
FIG. 19 is a perspective view showing a state in which the valve of FIG. 17 is removed from an associated mount piece.

FIGS. 17 to 19 show a valve 8 according to a seventh embodiment of the present invention. As shown in FIG. 17, the valve 8 has a bottomed cylinder U-shaped in cross section and a flange 37 formed on the outer periphery of the bottomed cylinder of the body 16 and engaged with an annular groove 36 provided in the inner wall of the mount piece 5. The valve 8 is fitted into the mount piece 5 as shown in FIG. 17.

A finger engaging tab 15 is provided integral with a portion of an upper end edge of the body 16 of the valve 8 such that it extends from the upper end edge of the body 16 of the valve 8. A cutout 38 is provided at one side of a base portion of the finger engaging tab 15. A groove 31 continuous with the cutout 38 is helically provided in the outer periphery of the body 16 such that it extends below the flange 37.

Upon an upward pull of the valve from a position in which it is fitted into the mount piece 5 as shown in FIG. 17 to a position shown in FIG. 18, the body 16 of the valve 8 is helically torn along the groove (weakened portion) 31 from the cutout 38 and the flange 3 fitted into the annular groove 36 of the mount piece is largely broken to an extent that the tab 15 can readily be pulled out of engagement with the mount piece 5. By pulling the tab 15 it is possible to readily remove the valve 8 from the mount piece. The used valve 8 is thus destroyed to an extent that it cannot again be attached to the mount piece. There is, therefore, no risk that the used valve 8 will again be used.

According to the seventh embodiment, no expanding force acts on the valve 8, unlike the first to third embodiments, when the valve is mounted in the mount piece 5. It is thus possible to prevent an unauthorized tearing of the valve 8 along its groove 31.

Figure 20:
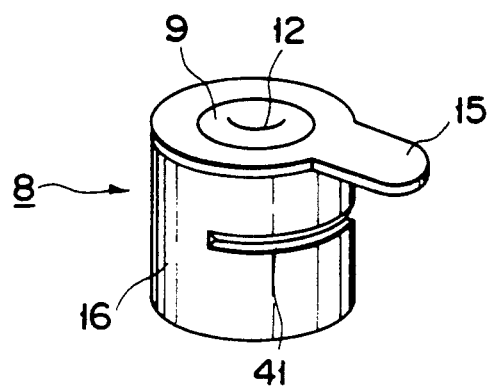
FIG. 20 is a perspective view showing a valve according to an eighth embodiment of the present invention.
Figure 21:
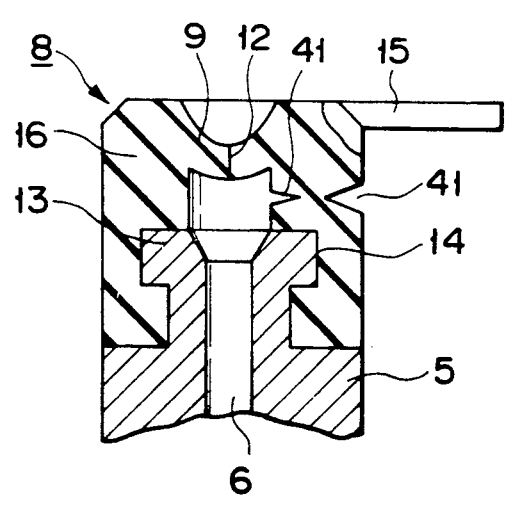
FIG. 21 is a cross-sectional view showing a state in which the valve of FIG. 20 is fitted over an associated mount piece.
Figure 22:
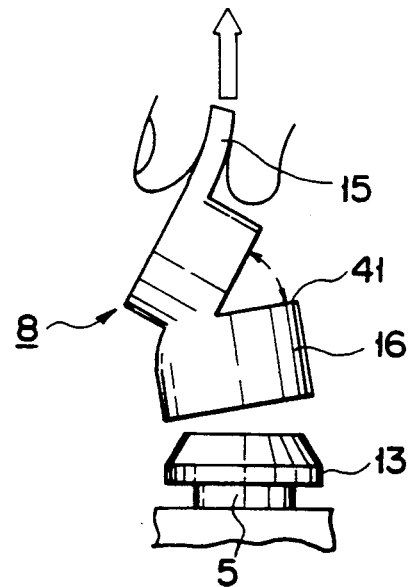
FIG. 22 is a side view showing a state in which the valve of FIG. 20 is removed from the mount piece.

FIGS. 20 to 22 show a valve 8 according to an eighth embodiment of the present invention. The valve 8 is formed of an elastic member, such as flexible plastics, as in the case of the aforementioned first embodiment. As shown in FIG. 21, a body 16 is M-shaped in cross-section. The body 16 has a closed film portion at its outer end portion with a slit 12 formed there to allow a treating instrument, not shown, or a treating unit such as a syringe, not shown, to be hermetically inserted through the closed film portion. An annular groove 14 is formed in the inner side wall of the valve 8 with a flange 13 of a mount piece 5 hermetically sealed there. A tongue-like tab 15 is provided, as a finger engaging section, at the edge of the upper end of the cylindrical side wall of the valve 8. The tab 15 is provided integral with the body 16 of the valve 8.

A pair of mutually opposite cuts 41, 41 are provided one at and around each side wall (that is, inner and outer side walls) of the valve 8 in a substantially semi-circular fashion. The cut 41 is provided in a position higher than that of the annular groove 14 as shown in FIG. 21, providing a weakened portion for breakage.

The valve 8 is normally fitted over the mount piece 5 of the endoscope 1 as shown in FIG. 21. A treating unit, for example, is hermetically inserted into an insertion channel 6 via the slit 12 of the valve 8.

The endoscope 1 is, for example, washed clean after it has been used and, at this time, the valve 8 is removed from the mount piece.

When the tab 15 is pulled upwardly by the operator's fingers, as indicated by an arrow in FIG. 22, upon the removal of the valve from the mount piece, the valve 8 is torn from the weakest portion 41 and, upon a further pull up of the tab, the annular groove 14 is removed from the outer periphery of the mating flange 13 through deformation.

Upon a further pull of the tab 15, the valve 8 is removed from the mount piece 5 in a "destroyed" state. That is, upon the removal of the valve 8 from the mount piece 5, the weakest portion is torn along the cuts 41 and the valve 8 is brought to a "broken" state. The so used valve 8 is broken to an extent that it cannot again be used. This ensures a sanitary safety.

A valve arrangement as shown in FIG. 23 may be adopted in the aforementioned embodiments. With t representing the thickness of a closed film portion having a slit 12, D, the inner diameter of a cylindrical body of the valve 8 and d, the diameter of the cylinder 43 of a syringe 42 which, when it is inserted through the slit 12, is defined at the opened end of the slit as shown in FIG. 23, the following relation is established:

$$2t + d < D$$

If this is done, it is possible to prevent the degeneration of the closed film portion 9 having the slit 12 during use. If, on the other hand $2t + d > D$, a damage or a tear occurs at the slit 12 of the closed film portion 9 when the forward end of the insertion cylinder 43 of the syringe 42 is inserted through the slit 12.

In a valve 8 shown in FIG. 25, a slit 12 has a closed film portion 9 with a tape 45, such as a red-color tape, stuck to the closed film portion 9. It is, therefore, necessary to peel the tape 45 off the closed film portion 9 when the valve 8 is used. Once the valve 8 is peeled off, the operator can know that the valve 8 is a "once-used" one.

The valve 8 as shown in FIG. 25 has two closed film portions having a slit 12. The outer closed film portion 9 is provided on a mount piece 47 which is detachably fitted over the cylindrical body 46. The mount piece 47 is provided integral with the cylindrical body 46 of the valve 8.

A caution mark 48 of "never use again" as shown in FIG. 25 is written on the outer peripheral surface of the valve's body with the use of a water-insoluble material and the caution mark is covered with a material 49 of the same color as that of the valve 8, in which case the material 49 is soluble in water.

If, for cleaning, the valve is dipped into water after it has been used, then the water-soluble material 49 is dissolved in the water so that the caution mark emerges. This prevents the reuse of the valve 8.

It is to be noted that the weakened portion may be provided by a plurality of apertures instead of using the grooves as set forth above.

Figure 27:
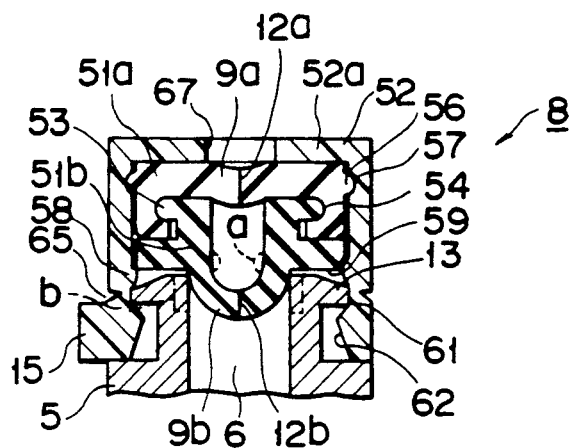
FIG. 27 is a cross-sectional view showing a state in which a valve according to a ninth embodiment of the present invention is fitted over an associated mount piece.
Figure 28:
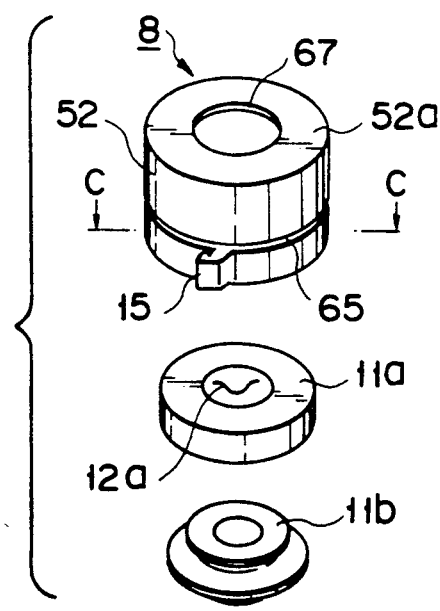
FIG. 28 is a perspective, exploded view showing the valve of the ninth embodiment.

FIGS. 27 to 30 show a valve according to a ninth embodiment of the present invention. FIG. 27 shows a state in which the valve 8 is attached to a mount piece of an endoscope.

The valve (assembly) 8 comprises a valve unit body 51a made of elastic material such as rubber, a valve unit body 51b made of elastic material such as rubber and a unit frame 51b made of relatively rigid synthetic material. The unit body 51b is formed of a cylindrical member closed at the lower end. The lower end portion provides a downwardly extending dome-like (semi-spherical) closed film portion 9b, noting that it is U-shaped as shown in FIG. 27. A slit 12b is formed at the center of the closed film portion 9b to allow an insertion portion of a treating unit such as a syringe to be hermetically inserted therethrough. Normally, the slit 12b is hermetically closed by an elastic force of the closed film portion 9b. A flange 53 is provided at the upper marginal edge of the unit body 51b to engage with the unit body 51a.

The unit body 51a is situated over the unit body 51b and an annular groove 54 is formed at the lower end portion of the unit body 51a with the flange 53 of the unit body 51b hermetically fitted therein. A closed film portion 9a is provided integral with the upper end portion of a body 9. A slit 12a is provided at the center of the closed film portion 9a to allow the insertion portion of, for example, the treating unit, such as syringe, to be hermetically inserted there-through. Normally, the slit 12a is hermetically closed by an elastic force of the closed film portion 9a.

The unit bodies 11a and 11b are arranged one over the other as shown in FIG. 27 to provide a valve body, in an assembled state, performing a valve function. The valve body is housed in, and held by, the unit frame 52 made of relatively rigid (semi-rigid) material as will be set forth below. The frame 52 is formed of a cylindrical member having an upper end wall 52a. An annular groove 57 is formed in the inner wall surface of the frame 52 to hermetically engage with an annular projection 56 formed on the outer peripheral surface of the unit body 51a. By so doing, the valve body is hermetically sealed in the unit frame. The annular groove 56, even if being formed on the outer peripheral surface of the unit body 51b, performs a similar sealing function.

An engaging projection 58 is provided on the inner wall surface of the frame 52 to hold the aforementioned valve body. The engaging projection 58 is so located that, upon fitting the annular projection 56 of the unit valve 51a into the annular groove 57 of the frame 52, the projection 58 engages with the lower end 59 of the unit body 51b.

The aforementioned valve body (including the unit bodies 51a and 52b) is assembled by forcing the unit bodies 51a and 52 up into the frame 52 with the lower open end of the frame 52 down and the unit body 51a placed over the unit body 51b so that the lower end face 59 of the unit body 51b latchingly engages with the projection 58 of the frame 52 at a location clear of the projection 58.

An annular groove 61 is hermetically fitted over a flange 61 of the endoscope's mount piece 5 at the inner wall surface of the frame 52 situated below the projection 58. The frame 52 has a diverging section 62 at an inner surface from the annular groove 61 to the lower end as shown in FIG. 27.

An annular cut groove 65 is formed in the outer peripheral surface of the frame 52 at a height substantially corresponding to the annular groove 61 formed in the inner wall surface of the frame 52. By so doing, it is possible to provide a weakened portion along the annular cut groove 65. As shown in FIGS. 27 to 30, a tongue-like tab 15 is projected on that outer peripheral surface of the frame 52 at a location below the annular cut groove 65. The knob 15 is provided integral with the frame 52.

Figure 29:
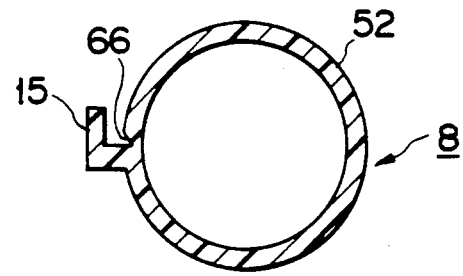
FIG. 29 is a cross-sectional view, taken long line C—C in FIG. 28.
Figure 30:
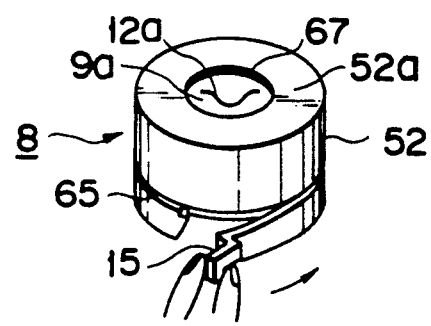
FIG. 30 is a perspective view showing a state in which the valve of the ninth embodiment is removed from the mount piece.

A cut groove 66 is formed at one side of a junction of the tab 15 and frame 52, as shown in FIG. 29, such that it extends in the axial (up/down) direction of the frame 52. The cut groove 66 merges with the annular cut groove 65 and extends toward the lower end of the frame 52 to provide a weakened portion along which the frame 52 is readily broken.

A hole 67 is provided at the top end wall 52a of the frame 52 to allow the insertion portion of, for example, a treating unit or a syringe to be inserted therethrough. Usually, the size of the hole 67 is so dimensioned as to substantially correspond to the external diameter of the insertion portion of the syringe.

In use, the valve 8 is forced on the mount piece 5 so that it is fitted over the mount piece through elastic deformation. After use, the valve 8 is pulled by the user's fingers in the circumferential direction indicated by an arrow in FIG. 30 and the frame is broken from the cut groove 66 toward the annular cut groove, that is, broken into upper and lower portions. It is thus possible to very readily remove the valve 8 from the mount piece 5 of, for example, an endoscope.

In this way, the frame 52 is fitted over the flange 13 of the endoscope's mount piece 5. Since the frame 52 is made of semi-rigid plastics, it is readily and positively snap-fitted over the mount piece's flange through the diverging section of the frame during use. The valve 8, once being fitted over the mount pieces flange, cannot be detached from there unless it is broken apart.

The valve can readily be removed from the associated mount piece by pulling the tab 15. At this time, the valve is broken to an extent that it is again not reused. This prevents the used or soiled valve from being reused, thus ensuring a sanitary safety.

Since the insertion hole 67 of the frame 52 is substantially equal to the diameter of the insertion portion of the syringe and the syringe, upon being inserted into the insertion hole 67, is so restricted as to be oriented at the center of the hole, there is less risk that the closed film portions 9a, 9b and slits 12a, 12b will be destroyed by the syringe.

Figure 31:
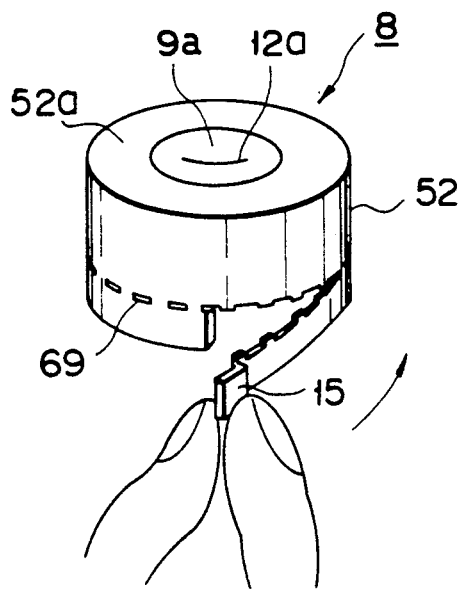
FIG. 31 is a perspective view showing a state in which a valve according to a tenth embodiment of the present invention is removed from an associated mount piece.

The weakened portion may be formed along perforations as shown in FIG. 31 so that the valve can be broken along the perforations.

A restriction portion, such as a projection, against which the forward end of the insertion portion of the syringe abuts, may be provided, for example, at the unit body 51 or 51b so that the insertion portion of the syringe may not be deeply inserted through the closed film portion as shown in FIG. 27. In this case, the insertion portion of the syringe is restricted by the restriction area a so that the insertion portion of the syringe is not inserted through the closed film portions 9a, 9b deeply to an unnecessary extent. By so doing, it is possible to prevent the closed film portions 9a, 9b, particularly the portion of the slit 12b, from being caught between the flange 13 of the mount piece 5 of the endoscope 1 and the forward end of the insertion portion of the syringe. It is thus possible to prevent a damage to the closed film portion 9b where the slit 12b is provided.

The marginal edge portion b of the open end of the flange 13 at the mount piece of the endoscope side, against which the closed film portion 9b abuts, may be formed by an elastic member as shown, for example, in FIG. 27. In this way it is possible to prevent the degeneration of the closed film portion 9b, particularly the slit 12b, caught between the flange 13 and the forward end portion of the insertion portion of the syringe.

When the forward end portion of the insertion portion of the syringe is inserted through the closed film portions 9a, 9b including the slits 12a, 12b, respectively, then the closed film portions 9a, 9b are spread open downwardly. The valve 8, particularly the closed film portion 9b of the body 51b in the aforementioned embodiment is so designed that the marginal edges of the slits 12a, 12b may not abut against the portion of the flange 13 of the endoscope's mount piece 5. For example, the closed film portion 9b including the slit the flange 13 (see FIG. 33) to be set forth below).

The unit bodies 51a, 51b may be formed as an integral unit or only one of them may serve the purpose.

FIG. 31 shows a tenth embodiment of the present invention. In the embodiment shown, a line of perforations is provided in a frame 52 in place of the aforementioned cut groove 65 so that the frame is broken along the line of perforations of the frame.

Figure 32:
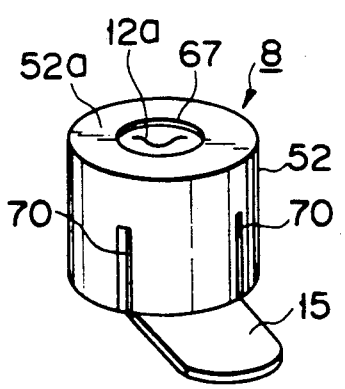
FIG. 32 is a perspective view showing a valve according to an eleventh embodiment of the present invention.
Figure 33:
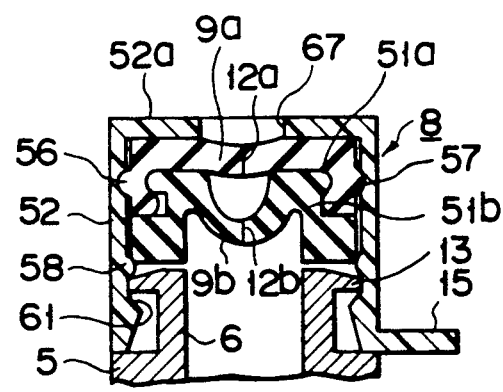
FIG. 33 is a cross-sectional view showing a state in which a valve according to the eleventh embodiment of the present invention is fitted over an associated mount piece.
Figure 38:
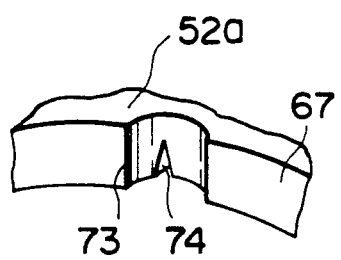
FIG. 38 is a perspective view showing a major part of the top wall of the valve of the thirteenth embodiment.
Figure 39:
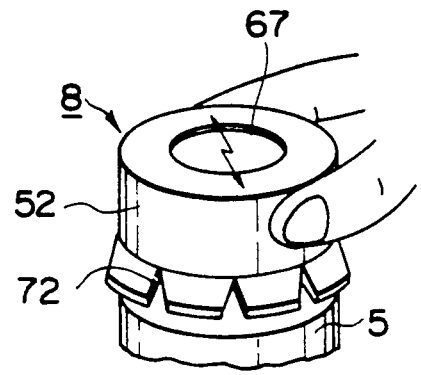
FIG. 39 is a perspective view showing a state in which the valve of the thirteenth embodiment is removed from an associated mount piece.

FIGS. 32 to 34 show a valve 8 according to an eleventh embodiment of the present invention.

In this valve 8, a tongue-like tab 15 provided at the lower end of the cylindrical side wall of the frame 52 such that it is formed integral with the frame 52. A pair of cut grooves 70 are provided in the outer periphery of the frame 52 such that they extends upward from both sides of a base portion of the tab to a level at least higher than that at which an annular groove 61 is situated. The other arrangement of the valve 8 is substantially the same as that of the aforementioned embodiment. As shown in FIG. 33, a closed film portion 9b of a unit body 51b is so constructed as to be spaced adequately from a flange 13 of a mount piece 5. Upon inserting the insertion end of the syringe through a slit 12b of the closed film portion 9b, the slit is spread open downwardly at which time the edge portion of the slit does not abut against the flange 13 of the endoscope's mount piece 13. Therefore, it is possible to prevent a damage to the closed film portion 9b having the slit 12 and hence to rapidly return the closed film portion 9b back to the original state.

Upon removing the valve from the mount piece as shown in FIG. 34, the tab 15 is pulled up by the operator's fingers. Then the cut groove 70 is torn upward from below so that a weakened portion is broken in a circular arc fashion along the cut groove. As a result, the valve 8 is readily removed from the mount piece 5 as indicated in FIG. 34. The other advantage is the same as already set forth above.

FIG. 35 shows a valve 8 according to a twelfth embodiment of the present invention.

A pair of perforation lines 69, 69 are formed in a frame 52 of the valve 8 in place of the aforementioned cut grooves 70, 70. A pull of the tab 15 causes a weakened portion to be torn along the pair of perforation lines 69, 69.

FIGS. 36 to 40 show a valve according to a thirteenth embodiment of the present invention.

In the valve 8 shown in FIG. 36, a plurality of cutouts 71 are formed at the lower end of the side wall of a frame 52. A corresponding plurality of cut grooves 72 are provided in the inner wall surface of the frame 52 in a manner to merge with the cutouts 71, and extend up vertically to a level higher than that at which an annular groove 61 of the frame 52 is situated.

Figure 40:
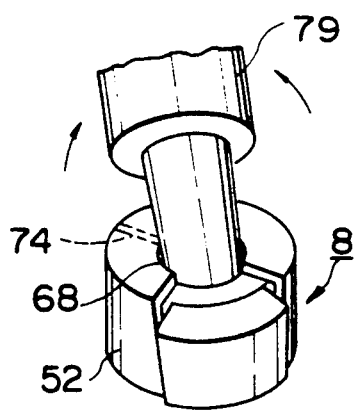
FIG. 40 is a perspective view showing a state in which the valve of the FIG. 39 is removed from the mount piece by another removal method.

A plurality of cutouts 73 are provided around the edge portion of an insertion hole 67 formed in the top wall 52a of the frame 52. A plurality of cut grooves 74 are provided in a manner to be continuous with the cutouts 73, and extend along the top wall surface of the frame down the side wall to the lower end of the frame as shown in FIG. 40. The other arrangement of the present embodiment is formed in the same fashion as set forth above.

The use of the valve 8 of the present embodiment will be explained below.

Upon removing the valve 8 from the associated mount piece 5, the valve 8 is pushed vertically in the longitudinal direction by the operator's fingers. Then such a vertical force acts upon the engaging portion of the frame with the mount piece 5, causing the frame 52 to be torn along the cut grooves 72 from the cutouts 71. As a result, the engaging lower end portion of the frame is spread apart so that the valve 8 is readily removed away from the mount piece 5. When, on the other hand, the insertion portion of the syringe is inserted through the insertion hole 67 in the top wall of the frame 52 and moved in the up/down and right/left directions as indicated by arrows in FIG. 40. Then a force acts upon the edge of the insertion hole 67, causing the frame 52 to be torn along the cut groove 74 from the cutouts 73 down to the lower end of the frame 52. As a result, the portion of the frame 52 is dropped down and the valve 8 is readily removed from the mount piece 5.

Since this valve 8 is not equipped with any tab, etc., the treating unit can be used freely without being hindered from such a projection during use. Upon the removal of the valve, it can readily be detached from the mount piece by moving the valve in any proper direction. There is also no need to grope for the tab which would otherwise be done so.

Conventionally, when the insertion portion of the syringe is inserted through the slit of the valve and moved in the front/back and right/left directions, the slit is often caught between the insertion portion of the syringe and the mount piece 13 and in a worst case there is a risk that the slit portion will be cut into fragments and the fragments will be dropped into an insertion channel. According to the present embodiment just set forth above, the frame 52 is separated away from the mount piece 5 before it is broken into fragments, preventing such an inconvenience as has encountered in the conventional valve. The other advantage is the same as set out above.

Needless to say, the valve 8 of such a type as to be held by the frame 52 can also be applied to the medical guide unit as shown in FIG. 10.

FIGS. 41 to 43 show a valve 8 according to a fourteenth embodiment of the present invention.

The valve 8 are composed of a unit of upper and lower bodies 51a and 51b made of elastic member, such as rubber. The valve unit is held within a frame 52 which is made of relatively hard material, such as synthetic resin, in comparison with the upper and lower bodies 51a and 51b.

The body 51b is formed of a substantially cylindrical member closed at the lower end. The closed bottom of the body 51b has a dome-like (semi-spherical) closed film portion 9b extending in the down direction. That is, the closed film portion 9b is U-shaped in ross-section as shown in FIG. 41. The closed film portion 9b has a slit 12b at the center through which the insertion portion of a treating unit or instrument is hermetically inserted. The slit 12 is hermetically closed by an elastic force of the closed film portion 9b and serves as what is called a valve. A flange 83 is formed on the upper marginal edge of the lower body 51b to engage with the upper body 51a.

A recess 85 is provided as a downwardly opened inner wall surface of the upper body 51a and hermetically fitted on the flange 83 of the lower body 51b. A closed film portion 9a is provided integral with the top wall of the upper body 51a. A slit 12a is provided at the center of the closed film portion 9a such that the insertion portion of a treating unit, such as a syringe, is hermetically inserted therethrough. The slit 12a is normally hermetically closed by an elastic force of the closed film portion 9a and serves as a valve through which the insertion portion of the treating unit is inserted.

The upper and lower bodies 51a and 51b are assembled into a mutually mated valve unit as shown in FIG. 41.

The valve unit is contained within the frame 52 such that it is hold by the frame 52. The frame 52 is formed as a substantially cylindrical member made of relatively rigid material (including a semi-rigid material). The frame 52 has a top end wall where a hole treating unit such as a syringe is inserted. The size of the hole 67 is so dimensioned as to correspond to the outer diameter of the insertion portion of the syringe which is substantially equal to the largest one of the treating units to be used.

A projection 58 is provided on the inner side wall surface of the frame 52 at a location shown in FIG. 41 such that it holds the valve unit within the frame 52 in a manner to support the lower surface portion of the edge portion of the lower body 51b.

A shoulder 84 is provided on the inner side wall surface of the frame 52 at a location below the engaging projection 58 to be latched to the flange 13 of the endoscope's mount piece 5. A downwardly diverging section 62 as shown in FIG. 41 is provided in the inner wall surface of the frame 52 and extends from the shoulder 85 toward the lower end of the frame 52.

With the frame 52 fitted over the endoscopie's mount piece as shown in FIG. 41, the marginal edge surface of the lower body 51b abuts against, and is hermetically sealed to, the marginal end face of the endoscopie's mount piece 5. For this reason, the open end of the endoscope's mount piece 5 is closed by the body 51b, that is, the valve unit. It is thus possible to provide a means whereby a sealing is achieved.

A tongue-like tab 15 integral with the frame 52 is provided at the lower end of the side wall of the frame 52 and slantwise extends in an outwardly downward direction with the lower end portion 86 somewhat inclined downwardly relative to the side wall of the frame 52. The tab 15 is gradually thickened from the forward end toward the side surface of the frame 52.

A weakened portion 87 for breakage is provided at both ends of a junction of the tab 15 and the frame 52 along the axial (up/down) direction of the frame 52. A pull of the tab 15 causes a ready breakage of the frame 52 along the weakened portion of the frame 52. The weakened portion 87 may be provided by a line of perforations. In other words, any proper weakened portion may be provided if being readily torn along the weakened line.

A pair of openings 88, 88 are provided at the side wall 52b of the frame 52 in a manner to be continuous with the weakened portion 87. The openings 88, 88 are opened to allow the interior of the frame 52 to be exposed to an outside atmosphere. The opening is formed as a slit along the axial (up/down) direction of the frame 52 and extends in line with the weakened portion 87 in a manner to merge with the latter portion.

A groove is provided along the outer peripheral portion of the side wall 52b in the proximity of the upper end of the side wall 52b of the frame 52 to merge with the two openings 88, offering a hinge portion 89.

At least one inspection hole 90 is formed in the side wall 52b of the frame 52 at a location near to the lower end of the lower frame 51b to make an inspection for proper mounting.

In use, the frame 52 is fitted over the flange 13 of the endoscope's mount piece 5 at the inner lower end portion of the frame. As will be seen from FIG. 41, the shoulder 85 is moved clear of the flange 13 downwardly, while being in cooperation with the downwardly diverging section 62, into latching engagement with the endoscope's mount piece. At that time, an inspection is made to see whether or not the bodies 51a, 51b are held in place within the frame 52.

In this way, the insertion portion of, for example, the treating unit or a syringe can hermetically be inserted into the valve.

After use, the valve is detached from the mount piece in the following way. First, the tab 15 is pulled up by the operator's finger as shown in FIG. 43. At this time, the tab 15 is swung in a direction of an arrow in FIG. 43 with the upper portion of that base portion as a fulcrum. At this time, the weakened portion 87 is torn relative to the mount piece by a force applied to the tab. The tab is completely opened wide along the weakened portion 87 and then along the openings 88, 88. For this reason, the tab thus wide-opened is further torn with the hinge portion 89 as a center upon a further pull of a small force this time. As a result, the tab 15 is torn wide-open from an initial position and the frame 52 is very readily removed away from the endoscope's mount piece 5.

In this way, the frame 52 is matingly fitted over the flange 13 of the endoscope's mount piece 5 and, in view of the fact that the frame 52 is made of the semi-rigid plastics, it is possible to readily and positively mount the valve on the mount piece by a small insertion force in cooperation with the downwardly diverging section 62.

The valve 8, once being mounted on the mount piece, cannot be removed from the mount piece unless it is broken apart. Upon the removal of the valve, the tab 15 is pulled up. In this case, the weakened portion 87 is torned from an initial position and then along the openings 88, 88 and opened wide at the side wall of the frame 52 to an extent that the frame cannot again be used.

For this reason, it is possible to prevent any insanitary reuse of the valve and to ensure a high level of safety.

The tab 15, being projected obliquely downward, is easy to finger-grip. Further, upon a pull of the tab 15 by the operator's fingers, the weakened portion 87 is very readily flexed because of the thickened base of the tab 15.

Since the valve bodies 51a, 51b are supported by the projection 58 formed on the inner surface of the frame 52, they are not separated from each other even when the valve 8 is removed from the endoscope's mount piece, thus ensuring a ready subsequent handling.

Figure 44:
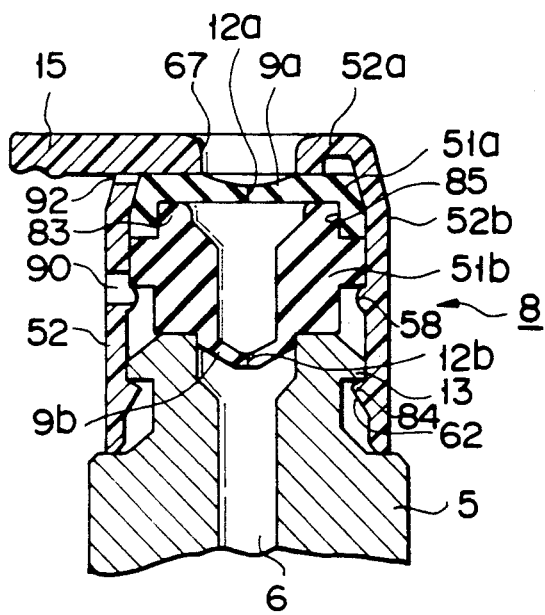
FIG. 44 is a cross-sectional view showing a valve according to a fifteenth embodiment of the present invention which is fitted over an associated mount piece.
Figure 45:
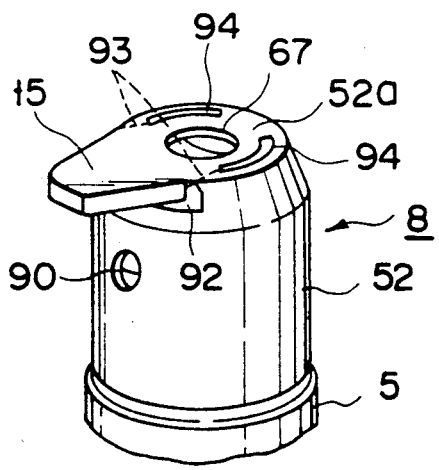
FIG. 45 is a perspective view showing a state in which the valve of FIG. 44 is fitted over the mount piece.
Figure 46:
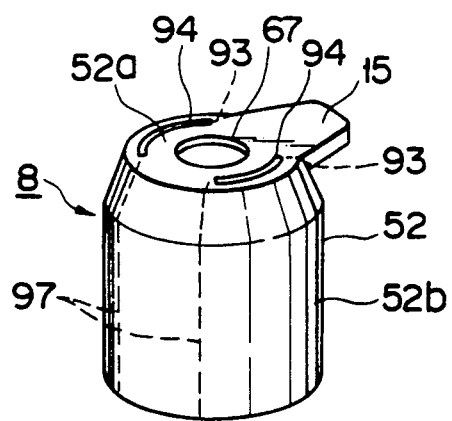
FIG. 46 is a perspective view showing a state when the valve is seen from the direction opposite to that shown in FIG. 45.

FIGS. 44 to 46 show a valve 8 according to a fifteenth embodiment of the present invention.

FIGS. 44 and 45 show the valve 8 mounted on the endoscope's mount piece 5 and FIG. 46 is a perspective view showing the back of the valve 8.

A frame 52 of the valve 8 is partially projected outwardly from its top wall to provide an integral tab 15. An opening 92 is provided at that lower top surface of the side wall of the frame situated adjacent the tab 15, providing a mechanical separation hole.

A first pair of weakened portions 93 for breakage are provided one at each side of the base portion of the tab 15 as shown in FIG. 45. A corresponding pair of arcuate slits 94 are provided relative to the associated weakened portions 93 to allow the inside of the frame 52 to communicate with an outer atmosphere. The arcuate slits are formed at the outer marginal edge portion of the top of the frame 52 in a diametrically opposite fashion with an insertion hole 67 as a center. The arcuate slit 94 is formed substantially in line with the weakened portion 94. The slits may be formed along the insertion hole 67 in an arcuate fashion.

As shown in FIG. 46, a second pair of weakened portions 97 are formed in the side wall 52 of the frame 52 along an axial direction in a parallel fashion with one end thereof situated in line with the associated end of the slit 94, the weakened portion extending down to the end (the other end) of the frame 52. The other arrangement is substantially the same as that of the fourteenth embodiment.

In use, the valve 8 is fitted over the mount piece 5 in the same fashion as set forth above.

After use, the valve 8 is removed from the mount piece by pulling up the tab 15 by the operator's fingers. In this case, the first weakened portions 93 are torned open by a pulling force relative to the slits 94, 94. In this way, a slight pull on the tab ensures a ready wide breakage of the frame along the first weakened portion 93.

When the upturned tab 15 or partly torn top wall 52a is further pulled, then the frame is further torn along the weakened portion 97 out of engagement with the mount piece 5. It is thus possible to readily remove the frame away from the mount piece 5.

As already set out above, the frame is torn open from the weakened portion 93 toward the slits 94 and then along the second weakened portions 97, 97, the added advantage of which will be as set forth below in comparison with the fourteenth embodiment. That is, in this embodiment, since the valve 8 cannot be detached from the mount piece 5 unless the frame is torn all along the weakened portions 93, 97, it is possible to positively prevent the reuse of the valve. Needless to say, the valve is not in an reusable condition even when the frame is broken open from the weakened portions 93 toward the slits.

The slits 94 may be replaced by weakened portions in the same way as the weakened portion 93. The valves 8 of the fourteenth and fifteenth embodiments can also be mounted on the mount piece 5 of the medical guide unit as already set forth above.

In the formation of weakened portions in the frame of the valve it may be possible to separate them from the rest of the frame of the valve and then bond them to the rest of the frame by a bonding agent. As the treating unit to be inserted via the valve, use may be made of a guide wire or a syringe. It is also possible to hermetically stab the syringe needle directly through a closed film portion with no slit. Various known types of closed film portions may be used for the valve of the present invention.

The valve of the present invention can be mounted on a channel mount piece of an electronic endoscope of such a type as to make an observation using a solid state image pickup device.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A valve assembly adapted to be fitted over a mount piece of a medical instrument whose distal end is inserted into a body cavity of a subject in cooperation with a treating unit, the valve assembly comprising:
   a body having first means formed of an elastic member and adapted to be opened when the treating unit is inserted therethrough and closed when the treating unit is removed therefrom, said body having a surrounding wall; and
   a frame for holding the body by its surrounding wall, said frame comprising second means detachably fitted over the mount piece, and third mean coupled to said second means for destroying the frame when the frame is removed from the mount piece;
   said third means comprising destruction means for making said second means in a not reusable state.

2. The valve assembly according to claim 1, wherein said third means comprises weakened lines formed in said frame.

3. The valve assembly according to claim 2, wherein said frame has a wall and said weakened lines are formed as thin-walled lines in the frame wall.

4. The valve assembly according to claim 2, wherein said frame has a wall and said weakened lines are formed as perforation lines in the frame wall.

5. The valve assembly according to claim 1, wherein said frame has a cylindrical wall and said third means is formed axially in the frame wall.

6. The valve assembly according to claim 1, wherein said frame has a cylindrical wall and said third means is formed helically in and along the cylindrical wall of the frame.

7. The valve assembly according to claim 1, further comprising a tab connected to said frame and adapted to be used when the frame is removed from said mount piece, and wherein said third means is formed in said frame in a continuous junction between said tab and said frame.

8. The valve assembly according to claim 1, wherein said third means comprises breaking lines formed in said frame and cutouts formed in a manner to merge with the breaking lines.

9. The valve assembly according to claim 1, wherein said second means comprises means for detachably fitting said body over a mount piece of an endoscope.

10. The valve assembly according to claim 1, wherein said second means comprises means for detachably fitting said body over a mount piece of a catheter.

11. The valve assembly according to claim 1, wherein said destruction means of said third means comprises first destroying means for destroying said frame when said frame is removed from said mount piece, second destroying means for destroying said frame when said frame is removed from said mount piece, and cutouts for connecting said first destroying means to said second destroying means.

12. The valve assembly according to claim 11, further comprising a tab provided on either one of said first and second destroying means.

13. A valve assembly adapted to be fitted over a mount piece of a medical instrument whose distal end is inserted into a body cavity of a subject in cooperation with a treating unit, the valve assembly comprising:

a body having first means formed of an elastic member and adapted to be opened when the treating unit is inserted therethrough and closed when the treating unit is removed therefrom, said body having a surrounding wall; and a frame for holding the body by its surrounding wall, said frame comprising second means detachably fitted over the mount piece, and third means for destroying the frame when the frame is removed from the mount piece;

said third means comprising means for making said third means in a not reusable state, said third means being provided in said frame.

14. The valve assembly according to claim 13, wherein said third means comprises weakened lines formed in said frame.

15. The valve assembly according to claim 14, wherein said frame has a wall and said weakened lines are formed as thin-walled lines in the frame wall.

16. The valve assembly according to claim 14, wherein said frame has a wall and said weakened lines are formed as perforation lines in the frame wall.

17. The valve assembly according to claim 13, wherein said frame has a cylindrical wall and said third means is formed axially in the frame wall.

18. The valve assembly according to claim 13, wherein said frame has a cylindrical wall and said third means is formed helically in and along the cylindrical wall of the frame.

19. The valve assembly according to claim 13, further comprising a tab connected to said frame and adapted to be used when the frame is removed from said mount piece, and wherein said third means is formed in said frame in a continuous junction between said tab and said frame.

20. The valve assembly according to claim 13, wherein said third means comprises breaking lines formed in said frame and cutouts formed in a manner to merge with the breaking lines.

21. The valve assembly according to claim 13, wherein said second means comprises means for detachably fitting said body over a mount piece of an endoscope.

22. The valve assembly according to claim 13, wherein said second means comprises means for detachably fitting said body over a mount piece of a catheter.

23. The valve assembly according to claim 13, wherein said destruction means of said third means comprises first destroying means for destroying said frame when said frame is removed from said mount piece, second destroying means for destroying said frame when said frame is removed from said mount piece, and cutouts for connecting said first destroying means to said second destroying means.

24. The valve assembly according to claim 13, further comprising a tab provided on one of said first and second destroying means.

* * * * *

UNITED STATES PATENT AND TRADEMARK OFFICE
CERTIFICATE OF CORRECTION

PATENT NO. : 5,104,379
DATED     : April 14, 1992
INVENTOR(S) : NAKAMURA et al

It is certified that error appears in the above-identified patent and that said Letters Patent is hereby corrected as shown below:

On the title page:
Under Section [30] Foreign Application Priority Data:

Replace "62-8946[U]" with --2-8946[U]--.

Under Section [56] References Cited, insert the following reference under "U.S. Patent Documents":

--4,610,665  9/1986  A. Matsumoto et al--.

Signed and Sealed this

Seventh Day of September, 1993

Attest:

BRUCE LEHMAN

*Attesting Officer*    *Commissioner of Patents and Trademarks*